United States Patent
Endoh

(10) Patent No.: US 11,298,094 B2
(45) Date of Patent: Apr. 12, 2022

(54) RADIOGRAPHY SYSTEM, PORTABLE INFORMATION TERMINAL, RADIOGRAPHY METHOD, AND COMPUTER-READABLE STORAGE MEDIUM

(71) Applicant: CANON KABUSHIKI KAISHA, Tokyo (JP)

(72) Inventor: Kenta Endoh, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 137 days.

(21) Appl. No.: 16/531,965

(22) Filed: Aug. 5, 2019

(65) Prior Publication Data
US 2019/0357867 A1 Nov. 28, 2019

Related U.S. Application Data

(63) Continuation of application No. PCT/JP2018/003479, filed on Feb. 1, 2018.

(30) Foreign Application Priority Data

Feb. 8, 2017 (JP) .............................. JP2017-021560

(51) Int. Cl.
*A61B 6/00* (2006.01)

(52) U.S. Cl.
CPC ............ *A61B 6/464* (2013.01); *A61B 6/4405* (2013.01); *A61B 6/463* (2013.01); *A61B 6/5294* (2013.01)

(58) Field of Classification Search
CPC ........... A61B 6/00; A61B 6/463; A61B 6/465; A61B 6/548; A61B 6/4405; A61B 6/464;
(Continued)

(56) References Cited

U.S. PATENT DOCUMENTS

| | | | |
|---|---|---|---|
| 2002/0080918 A1* | 6/2002 | Sako | A61B 6/548 378/115 |
| 2010/0169423 A1 | 7/2010 | Eguchi | |

(Continued)

FOREIGN PATENT DOCUMENTS

| | | |
|---|---|---|
| JP | 2008178578 A | 8/2008 |
| JP | 2014117398 A | 6/2014 |

(Continued)

OTHER PUBLICATIONS

International Search Report dated Mar. 6, 2018 in corresponding International Patent Application No. PCT/JP2018/003479.

(Continued)

*Primary Examiner* — Dani Fox
(74) *Attorney, Agent, or Firm* — Carter, DeLuca & Farrell LLP

(57) ABSTRACT

A radiography system is provided such that a plurality of portable information terminals are associated with a radiation detecting unit so as to be managed by a processing unit. This improves portability and facilitates management including a change of association. The radiography system includes a radiation detecting unit arranged to detect radiation, a plurality of portable information terminals allowed to be associated with the radiation detecting unit, and a processing unit configured to receive and process radiographic image data detected by the radiation detecting unit and transmit the processed radiographic image data to the portable information terminal associated with the radiation detecting unit.

18 Claims, 12 Drawing Sheets

(58) Field of Classification Search
CPC ....... A61B 6/468; A61B 6/5294; A61B 6/545; A61B 6/536; A61B 6/36
See application file for complete search history.

(56) References Cited

U.S. PATENT DOCUMENTS

2017/0360390 A1* 12/2017 Tajima .................... A61B 6/56
2019/0231295 A1    8/2019 Kawanishi et al.
2019/0235093 A1    8/2019 Tanaka et al.

FOREIGN PATENT DOCUMENTS

| JP | 2015173803 A | 10/2015 |
| JP | 2015177988 A | 10/2015 |
| JP | 2015191555 A | 11/2015 |
| JP | 2016034470 A | 3/2016 |
| JP | 2017501459 A | 1/2017 |
| WO | 2011163660 A | 12/2011 |
| WO | 2013153801 A | 10/2013 |
| WO | 2015048302 A | 4/2015 |
| WO | 2016136415 A1 | 9/2016 |

OTHER PUBLICATIONS

International Preliminary Report on Patentability issued by the International Bureau in corresponding International Application No. PCT/JP2018/003479 dated Aug. 22, 2019, with English translation.
Notice of Reasons for Refusal issued by the Japan Patent Office dated Jul. 2, 2020 in corresponding JP Patent Application No. 2017-021560, with English translation.
Examination Report issued by the GB Intellectual Property Office dated Oct. 5, 2021 in corresponding GB Patent Application No. 1911283.8.

\* cited by examiner

RADIOGRAPHY SYSTEM, PORTABLE INFORMATION TERMINAL, RADIOGRAPHY METHOD, AND COMPUTER-READABLE STORAGE MEDIUM

CROSS-REFERENCE TO RELATED APPLICATIONS

This application is a Continuation of International Patent Application No. PCT/JP2018/003479, filed Feb. 1, 2018, which claims the benefit of Japanese Patent Application No. 2017-021560, filed Feb. 8, 2017, all of which are hereby incorporated by reference herein in their entirety.

BACKGROUND OF THE INVENTION

Field of the Invention

The present invention relates to a radiography system, a portable information terminal, a radiography method, and a computer-readable storage medium.

Description of the Related Art

In a radiography system including a typical radiography apparatus, the radiography apparatus is configured to operate while a console including a computer controls radiography. When radiography is performed, it is always necessary to arrange a set of a radiation generator, the radiography apparatus, and the control console. Moreover, the control console is a device requiring high performance because it takes a long time for image processing or the like.

In recent years, configurations for using portable information terminals such as a tablet have been proposed to improve usability (for example, Japanese Patent Application Laid-Open No. 2016-34470). For example, a radiation generator, a control console, and a wireless access point are installed on a medical cart. The wireless access point constitutes a network wirelessly connecting a radiography apparatus, the console, and a portable information terminal. The console is essential for the function of the portable information terminal.

The prior art has problems to be solved. The first problem is a reduction in portability. In view of the processing resource of the portable information terminal, it is necessary to use the portable information terminal as a unit accompanying the single console. Thus, if multiple portable information terminals are used, the number of consoles (units) increases with the number of portable information terminals, thereby reducing the portability.

The second problem is that the apparatus is associated in a complicated manner. The radiography apparatus and the portable information terminal are managed by each console. Thus, if the apparatus is to be controlled by another console, it is necessary to change the association with the console, leading to a complicated changing operation.

SUMMARY OF THE INVENTION

A radiography system according to the present invention includes a radiation detecting unit arranged to detect radiation, a plurality of portable information terminals allowed to be associated with the radiation detecting unit, and a processing unit configured to receive and process radiographic image data detected by the radiation detecting unit and transmit the processed radiographic image data to the portable information terminal associated with the radiation detecting unit.

Further features of the present invention will become apparent from the following description of exemplary embodiments with reference to the attached drawings.

DESCRIPTION OF THE EMBODIMENTS

Preferred embodiments of the present invention will be specifically described below with reference to the accompanying drawings. The following embodiments do not limit the invention according to claims. All the combinations of features according to the embodiments are not always necessary for the solver of the invention.

First Embodiment

Figure 1:
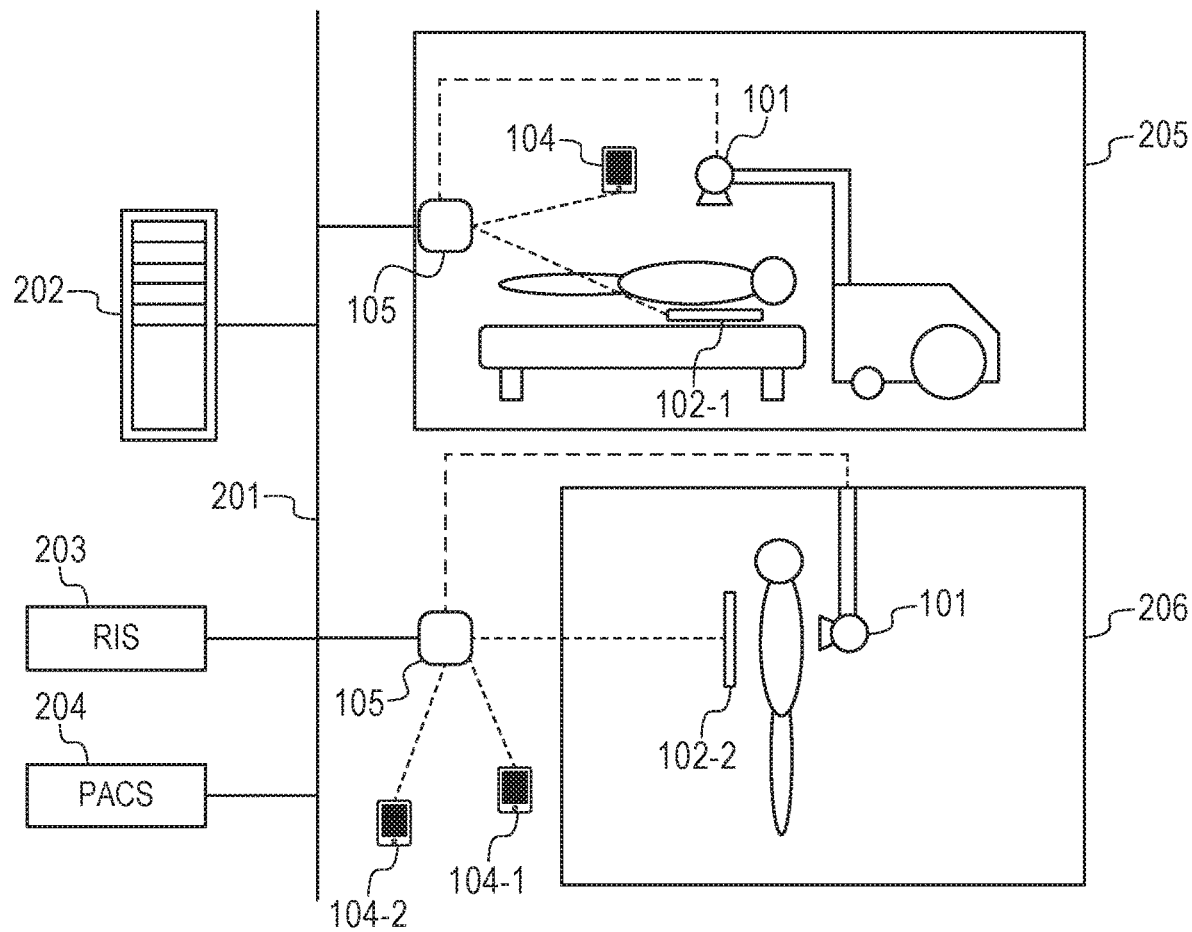
FIG. 1 is a configuration diagram illustrating an example of a radiography system according to a first embodiment of the present invention.

FIG. 1 is a configuration diagram illustrating an example of a radiography system according to a first embodiment of the present invention.

As illustrated in FIG. 1, a radiation generator (radiation generating unit) 101 that generates radiation, a radiography apparatus (radiation detecting unit) 102 that detects radiation, and a portable information terminal 104 are connected to a network 201 via a wireless access point 105. Multiple portable information terminals 104-1 and 104-2 can be associated with a radiography apparatus (radiation detecting unit) 102-2. If it is not necessary to distinguish between the portable information terminals 104-1 and 104-2 and between a radiography apparatus 102-1 and the radiography apparatus 102-2, the portable information terminals will be simply referred to as the portable information terminal 104 and the radiography apparatuses will be simply referred to as the radiography apparatus 102.

A central processing apparatus (processing unit) 202 is connected to the network 201, performs image processing on a radiographic image transmitted from the radiography apparatus 102, and transmits the radiographic image to the associated portable information terminal 104. The central processing apparatus 202 receives and processes radiographic image data detected by the radiography apparatus 102 and transmits the processed radiographic image data to the portable information terminal 104 associated with the radiography apparatus 102.

The portable information terminal 104 can be associated with the radiography apparatus 102 that detects radiation. The portable information terminal 104 receives the processed radiographic image data from the central processing apparatus 202 that processes the radiographic image data detected by the radiography apparatus 102.

Furthermore, RIS (Radiology Information Systems) 203 and PACS (Picture Archiving and Communication Systems) 204 are connected to the network 201. This enables the central processing apparatus 202 or the like to transmit and receive data to and from the RIS 203 and the PACS 204 via the network 201.

FIG. 1 illustrates configurations for shooting in a doctor's round visit to a sickroom 205 and shooting in a general radiological room 206. These configurations do not limit the application of the present invention. The network 201 connecting each device is not limited to a hospital LAN. The central processing apparatus 202, the RIS 203, and the PACS 204 may be connected to external cloud service.

Figure 2:
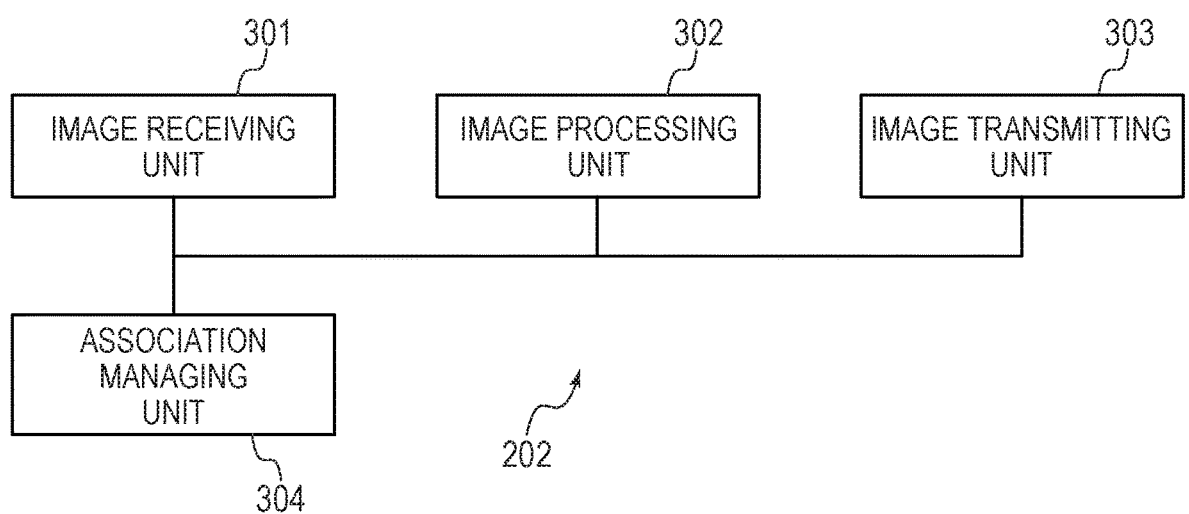
FIG. 2 is a block diagram illustrating an example of a functional configuration diagram of a central processing apparatus.

FIG. 2 is a block diagram illustrating an example of a functional configuration diagram of the central processing apparatus 202. An image receiving unit 301 receives radiographic images transmitted from the radiography apparatuses 102-1 and 102-2 and outputs the images to an image processing unit 302. The image processing unit 302 performs image processing on the radiographic images and outputs the processed images to an image transmitting unit 303.

The image transmitting unit 303 specifies the portable information terminal 104 as a destination associated with the source (radiography apparatus 102) of the radiographic image, from the association between the radiography apparatus 102 and the portable information terminal 104. The association is stored in advance in an association managing unit (associating unit) 304. The image transmitting unit 303 transmits the processed image to the associated portable information terminal 104.

Figure 3:
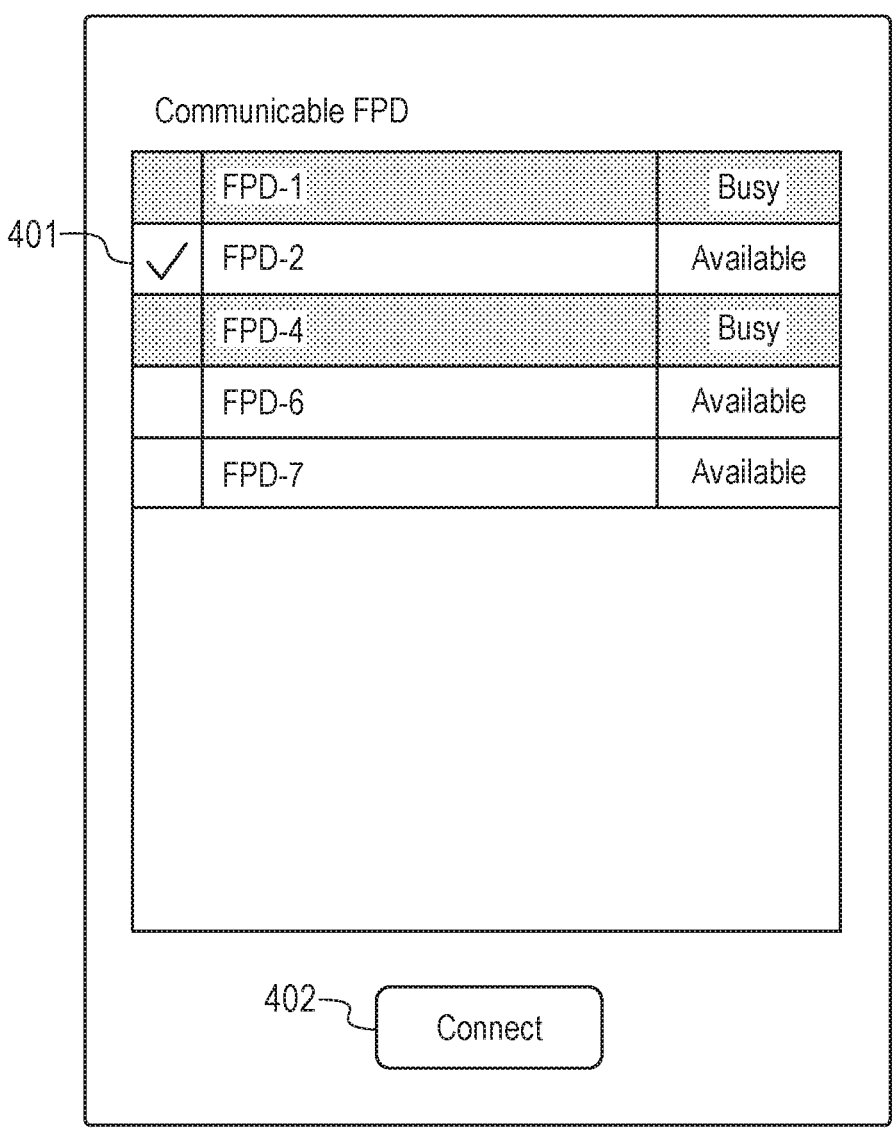
FIG. 3 illustrates an example of a GUI displayed on a portable information terminal.

FIG. 3 illustrates an example of a GUI displayed on the portable information terminal 104. The GUI is provided to select the radiography apparatus 102 associated with the portable information terminal 104. The portable information terminal 104 displays the radiography apparatuses 102 that can be associated with the portable information terminal 104 and selects the radiography apparatus 102 associated with the portable information terminal 104. In this case, an FPD (Flat Panel Detector) is used as an example of the radiography apparatus 102.

The radiography apparatuses 102 connected to the network 201 are displayed on a connectable radiography apparatus list 401. The items of the radiography apparatuses on the radiography apparatus list 401 indicate statuses such as "busy" and "available". By pressing a connecting button 402, the portable information terminal 104 and the radiography apparatus 102 are associated with each other.

If the portable information terminal 104 is to be associated with another radiography apparatus, the GUI screen may be restored to select the desired radiography apparatus 102.

Figure 4:
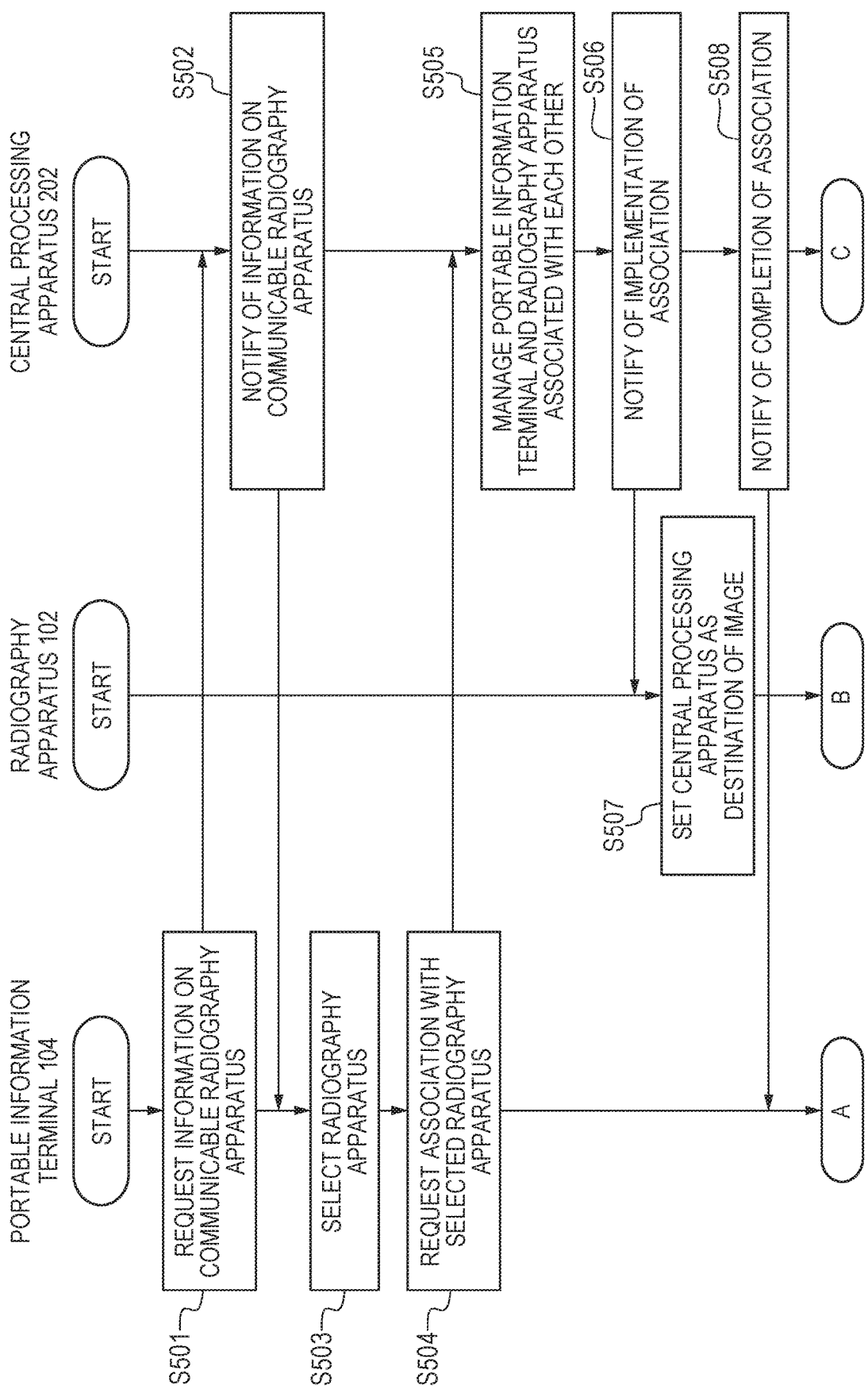
FIG. 4 is a flowchart showing an example of the association processing between the portable information terminal and a radiography apparatus.

FIG. 4 is a flowchart showing an example of the association processing between the portable information terminal 104 and the radiography apparatus 102.

The portable information terminal 104 requests information on the communicable radiography apparatuses 102 from the central processing apparatus 202 (step S501). In response to the request, the central processing apparatus 202 notifies the portable information terminal 104 of information on the radiography apparatuses 102 connected to the network 201 (step S502). The portable information terminal 104 displays the connectable radiography apparatus list 401. An operator selects the radiography apparatus 102 to be associated with the portable information terminal 104 from among the "available" radiography apparatuses 102 in the radiography apparatus list 401 (step S503).

When the radiography apparatus 102 is selected, the portable information terminal 104 requests association with the selected radiography apparatus 102 from the central processing apparatus 202 (step S504). In response to the request, the association managing unit 304 associates the selected radiography apparatus 102 and the portable information terminal 104 and then manages the association (step S505). The association managing unit 304 manages the radiography apparatus 102 that can be associated with the portable information terminal 104 and associates the radiography apparatus 102 and the portable information terminal 104 in response to the request for the association from the portable information terminal 104.

The radiography apparatus 102 is notified of the implementation of the association (step S506). The radiography apparatus 102 sets the address of the central processing apparatus 202 as a destination of a radiographic image (step S507). The central processing apparatus 202 notifies the portable information terminal 104 of the completion of processing (step S508). In this way, the connection between the portable information terminal 104 and the radiography apparatus 102 is established.

In the present embodiment, the "available" radiography apparatus 102 is selected. In this system, however, the portable information terminal 104 may select the "busy" radiography apparatus 102 so as to acquire the right to use the "busy" radiography apparatus 102 and associate the radiography apparatus 102 with the portable information terminal 104. In this case, in order to acquire the right to use, a request for the right to use may be sent from the central processing apparatus 202 to the radiography apparatus 102.

At the completion of shooting of a radiographic image by the radiography apparatus 102, the association between the radiography apparatus 102 and the portable information terminal 104 may be canceled and the status of the radiography apparatus 102 may be changed from "busy" to "available". If the radiography apparatus 102 is not operated for a predetermined time, the association between the radiography apparatus 102 and the portable information terminal 104 may be canceled and the status of the radiography apparatus 102 may be changed from "busy" to "available".

If the radiography apparatus 102 is turned off, the association between the radiography apparatus 102 and the portable information terminal 104 may be canceled and the status of the radiography apparatus 102 may be changed from "busy" to "available". If the radiography apparatus 102 and the network 201 are disconnected from each other, the association between the radiography apparatus 102 and the portable information terminal 104 may be canceled and the status of the radiography apparatus 102 may be changed from "busy" to "available".

Alternatively, an operation of the portable information terminal 104 may forcibly cancel the association between the radiography apparatus 102 and the portable information terminal 104 and the status of the radiography apparatus 102 may be changed from "busy" to "available".

As described above, in at least one of a case where the shooting of a radiographic image by the radiography apparatus 102 is completed, a case where the radiography apparatus 102 is not operated for the predetermined time, a case where the radiography apparatus 102 is turned off, and a case where the network connection of the radiography apparatus 102 is cut off, the association between the radiography apparatus 102 and the portable information terminal 104 is canceled.

Conventionally, multiple portable information terminals were not associated with the same radiography apparatus, whereas in the present embodiment, the portable information terminals 104 are associated with the same radiography apparatus 102 and are operated as a single unit. For example, as illustrated in FIG. 1, multiple portable information terminals 104-1 and 104-2 are associated with the same radiography apparatus 102-2. Moreover, in the present embodiment, the first portable information terminal 104-1 of multiple portable information terminals 104 can control the association of the second portable information terminal 104-2 with the radiography apparatus 102.

The first portable information terminal 104-1 associated with a radiation detecting unit can control the association between the radiography apparatus 102 and the second portable information terminal 104-2. For example, the first portable information terminal 104-1 can cancel the association between the radiography apparatus 102 and the second portable information terminal 104-2.

Figure 5:
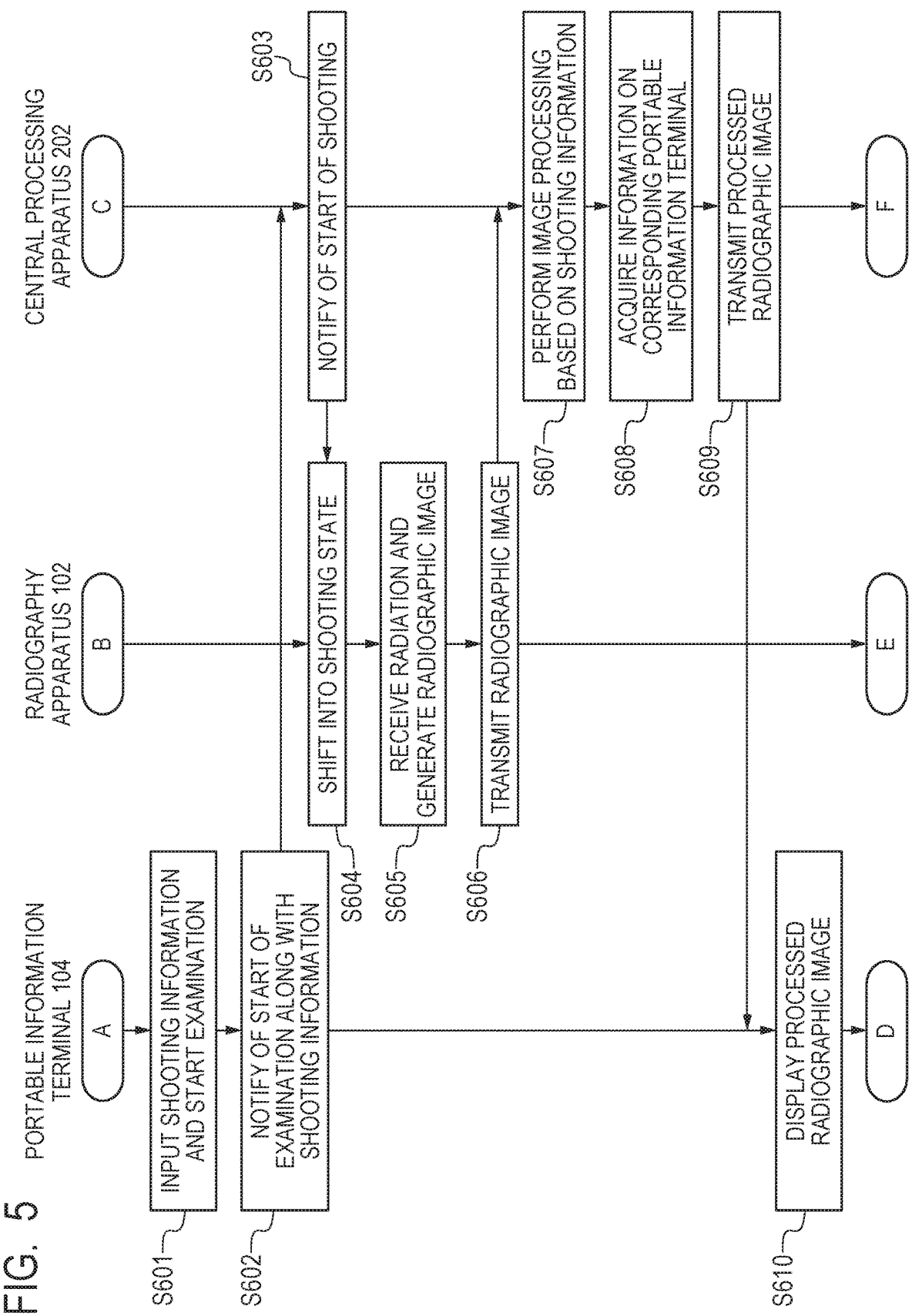
FIG. 5 is a flowchart showing an example of processing in which a radiographic image captured by the radiography apparatus is displayed on the portable information terminal.

FIG. 5 is a flowchart showing an example of processing in which a radiographic image captured by the radiography apparatus 102 is displayed on the portable information terminal 104 after the association is completed.

The operator inputs shooting information on a patient' name, a part, and a shooting direction to the portable information terminal 104 and starts an examination (step S601). The portable information terminal 104 notifies the central processing apparatus 202 of the start of examination along with the inputted shooting information (step S602). The central processing apparatus 202 notifies the radiography apparatus 102 of the start of shooting (step S603). The radiography apparatus 102 having received the start of shooting shifts into a shooting state and waits for radiation emission (step S604).

Upon radiation emission, the radiography apparatus 102 generates a radiographic image (step S605). The generated radiographic image is transmitted to the central processing apparatus 202 set as a destination of the image (step S606). The central processing apparatus 202 performs proper image processing on the received radiographic image based on the shooting information received in step S602 (step S607). The central processing apparatus 202 acquires information on the portable information terminal 104 associated with the radiography apparatus 102 having transmitted the radiographic image, from the association managing unit 304 (step S608).

The central processing apparatus 202 transmits the radiographic image, which has undergone the image processing, to the portable information terminal 104 based on the information on the portable information terminal 104 (step S609). The portable information terminal 104 receives the processed radiographic image and displays the image (step S610).

As described above, in response to an image transmission request from the portable information terminal 104 associated with the radiography apparatus 102, the central processing apparatus 202 transmits the processed radiographic image to the portable information terminal 104. The radiographic image is obtained by performing predetermined image processing on the radiographic image outputted from the radiography apparatus 102. In other words, the central processing apparatus 202 transmits the radiographic image data processed by the central processing apparatus 202 to the portable information terminal 104.

Moreover, in response to the image transmission request from the portable information terminal 104 associated with the radiography apparatus 102, the central processing apparatus 202 may transmit, to the portable information terminal 104, radiographic image data outputted from the radiography apparatus 102 or radiography image data intermediately generated in the process of the central processing apparatus 202.

In the present embodiment, multiple portable information terminals 104 are associated with the same radiography apparatus 102 and are operated as a single unit. The central processing apparatus 202 can allocate data to the portable information terminals 104 based on the information on the portable information terminal 104, the information being obtained in step S608.

In the present embodiment, the central processing apparatus 202 includes the association managing unit 304. Alternatively, however, the radiography apparatus 102 may include the association managing unit 304 and identify and manage the portable information terminal 104 associated with the radiography apparatus 102. The association managing unit 304 manages the radiography apparatus 102 that can be associated with the portable information terminal 104 and outputs a command for associating the radiography apparatus 102 and the portable information terminal 104 in response to the request for the association from the portable information terminal 104.

In this case, the radiography apparatus 102 transmits the address (information) of the associated portable information terminal 104 as additional information to the central processing apparatus 202 along with the radiographic image and notifies the central processing apparatus 202 of the information on the portable information terminal 104 serving as the destination of step S609.

The portable information terminal 104 may be associated with multiple radiography apparatuses 102. For example, if multiple radiography apparatuses of varying sizes are exchanged or multiple radiography apparatuses are arranged in a row in an examination on the same sample, multiple radiography apparatuses 102 are associated with the portable information terminal 104. If the radiography apparatuses are arranged in a row, the central processing apparatus 202 may composite radiographic images captured by multiple radiography apparatuses 102 and transmit the composited radiographic images to the portable information terminal 104 associated with the radiography apparatuses 102.

Second Embodiment

In the first embodiment, it is described that the portable information terminal 104 displays a radiographic image when the radiographic image is shot. In a second embodiment, it will be described that a portable information terminal 104 redisplays a radiographic image captured in the past.

Figure 6:
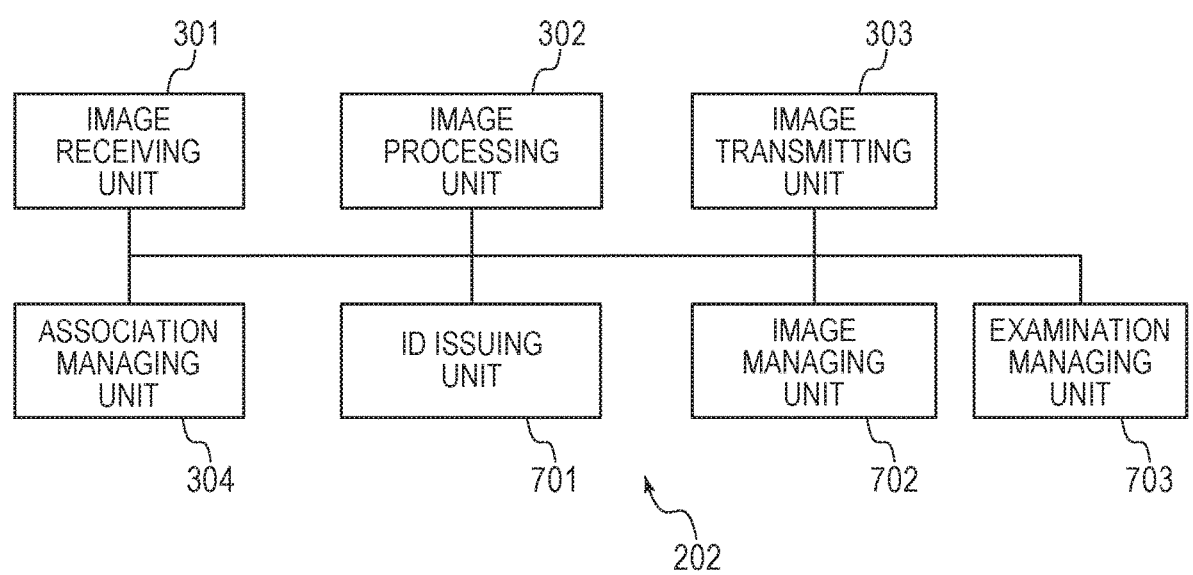
FIG. 6 is a block diagram illustrating an example of a functional configuration diagram according to a second embodiment of the present invention.

FIG. 6 is a block diagram illustrating an example of a functional configuration diagram of the second embodiment. An ID issuing unit 701 issues an image ID to a radiographic image. The ID issuing unit 701 issues an image ID to radiographic image data detected by a radiography apparatus 102 or processed radiographic image data. An image managing unit 702 stores and manages a received radiographic image and an image ID that are associated with each other. The image managing unit 702 manages radiographic image data or processed radiographic image data that is associated with an image ID. An examination managing unit 703 manages examination information, e.g., patient information, etc. and an image ID that are associated with each other.

The radiographic image managed by the image managing unit 702 is not limited to a radiographic image outputted from the radiography apparatus 102. A radiographic image having undergone predetermined image processing may be managed instead. If image processing is performed in multiple steps, an intermediate radiographic image may be managed instead. Alternatively, the image managing unit 702 may manage two or more of the radiographic image outputted from the radiography apparatus 102, the radiographic image having undergone the predetermined image processing, and the intermediate radiographic image generated in the process of image processing.

In this case, the series of radiographic images is managed with the same image ID. The image managing unit 702 manages the radiographic image outputted from the radiography apparatus 102, the radiographic image having undergone the predetermined image processing, and the intermediate radiographic image generated in the process of image processing, the radiographic images being associated with the same image ID.

Figure 7:
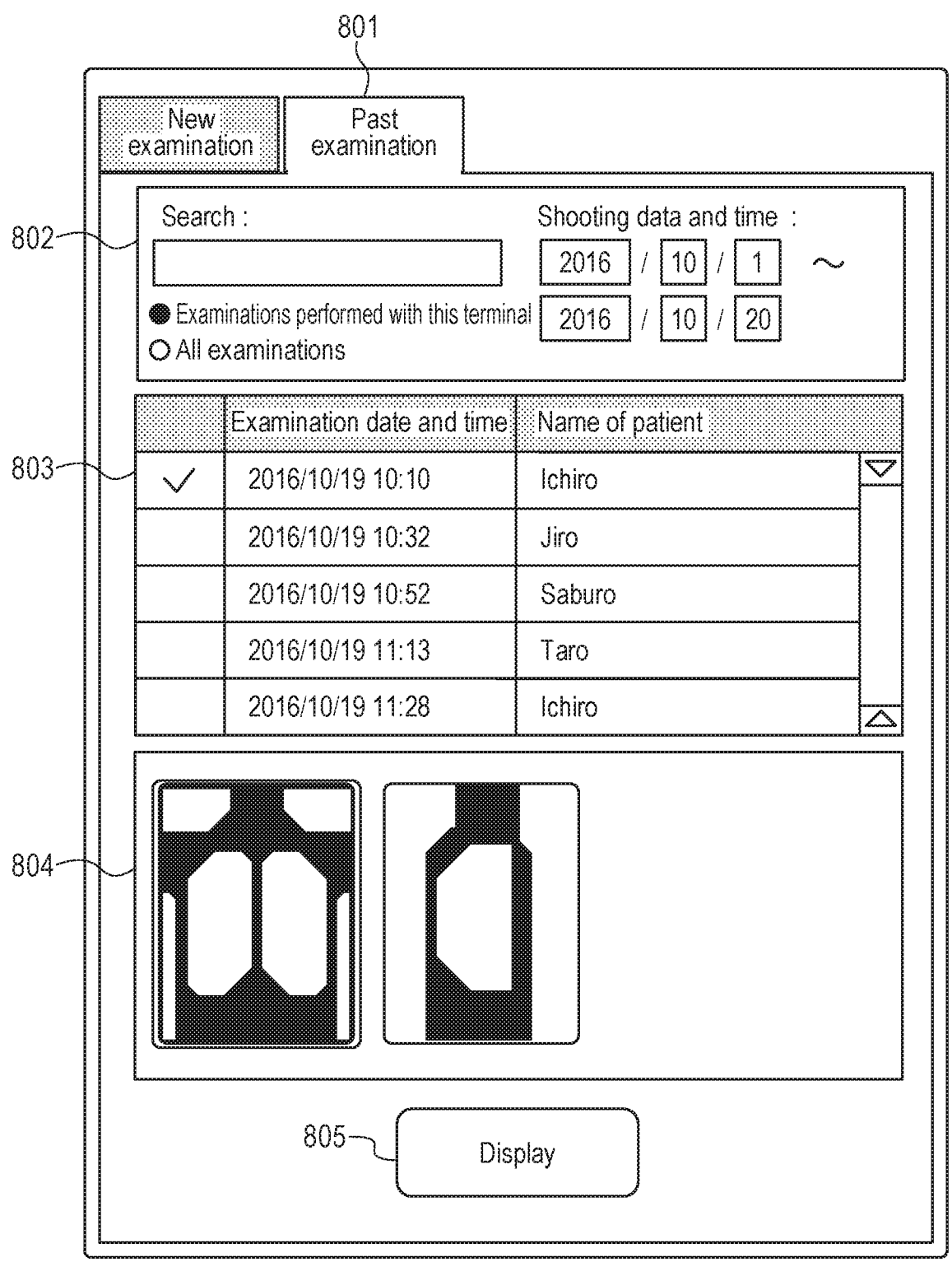
FIG. 7 illustrates an example of a GUI (a display/selection screen of examinations captured in the past) displayed on the portable information terminal.

FIG. 7 illustrates an example of a GUI (a display/selection screen of examinations captured in the past) displayed on the portable information terminal 104.

An examination tab 801 displays the GUI that selects completed examinations by picking up past examinations. A search filter 802 can filter examinations in a past examination list 803 in response to an input of a character string or selection of choices. When an examination is selected from the past examination list 803, the thumbnail of a radiographic image captured in the past examination is displayed in a thumbnail list 804. When an image is selected from the thumbnail list 804 and a display button 805 is pressed, the redisplay of the captured radiographic image is started.

FIG. 7 illustrates the GUI for displaying a radiographic image selected from the thumbnail list 804. The GUI is not particularly limited. An examination may be selected so as to display the first radiographic image of the examination.

Figure 8:
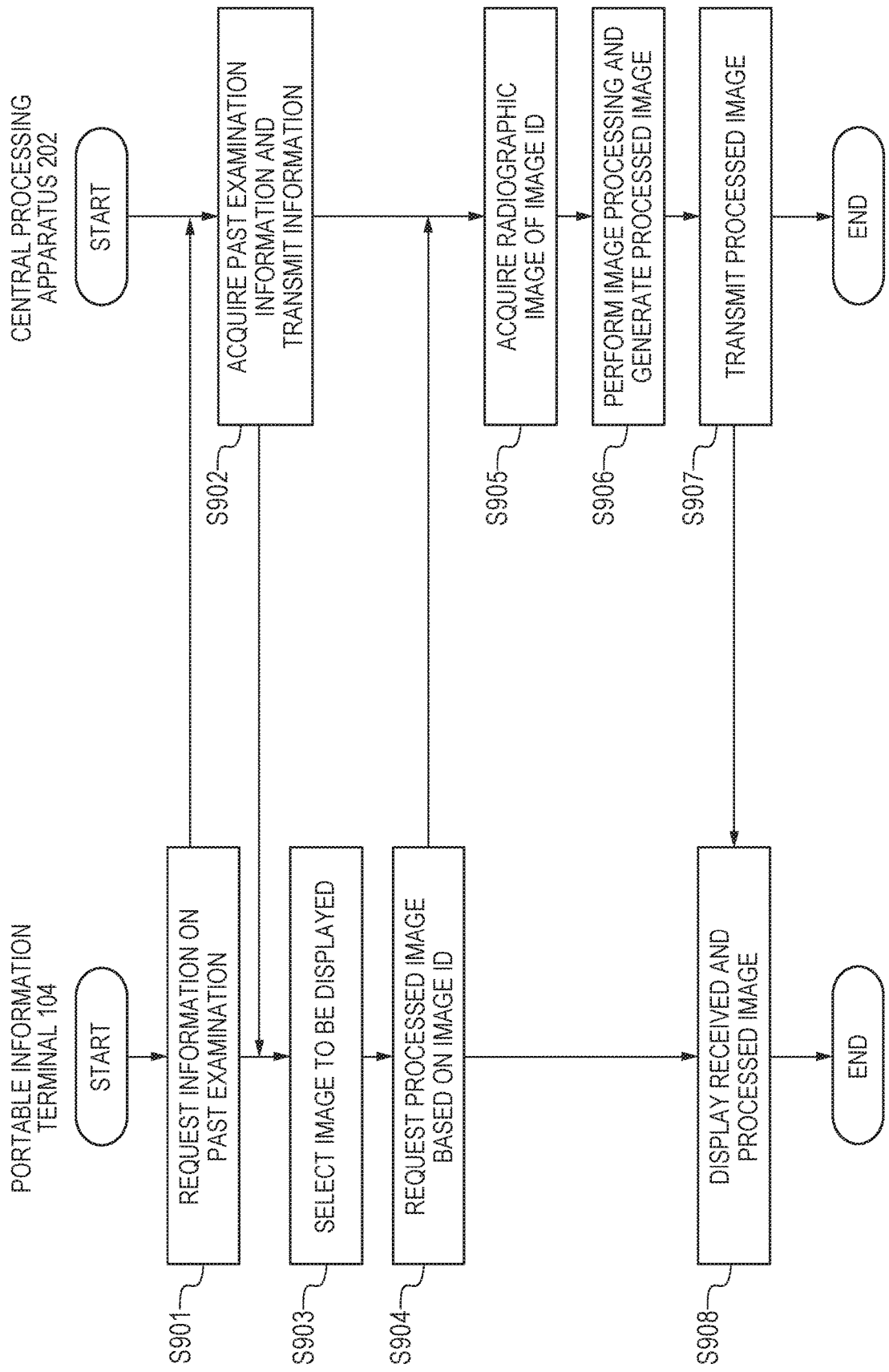
FIG. 8 is a flowchart showing an example of a processing flow of redisplaying a past radiographic image.

FIG. 8 is a flowchart showing an example of a processing flow of redisplaying a past radiographic image. When a past examination is selected from the examination tab 801, the portable information terminal 104 requests information on the examination performed in the past from a central processing apparatus 202 (step S901). The central processing apparatus 202 acquires, from the examination managing unit 703, thumbnail images and examination information (e.g., patient information) associated with an examination matching the conditions of the request. The central processing apparatus 202 then transmits the examination information and the thumbnail images to the portable information terminal 104 (step S902).

The portable information terminal 104 displays the examination information in the past examination list 803. An operator selects an examination to be viewed, selects an image to be viewed from the thumbnail list 804, and then presses the display button 805 (step S903). The portable information terminal 104 requests a radiographic image processed to be redisplayed, from the central processing apparatus 202 based on an image ID associated with the selected thumbnail (step S904). In this way, the portable information terminal 104 associated with the radiography apparatus 102 transmits the image transmission request to the central processing apparatus 202 based on the past examination information.

In response to the request, the central processing apparatus 202 acquires the radiographic image of the specified image ID from the image managing unit 702 (step S905). The central processing apparatus 202 performs image processing on the radiographic image again based on an image processing parameter stored as the examination information, and generates a processed radiographic image (step S906). The central processing apparatus 202 transmits the processed radiographic image to the portable information terminal 104 (step S907). The central processing apparatus 202 performs image processing on radiographic image data according to a parameter set as the examination information and transmits the radiographic image data having undergone the image processing to the portable information terminal 104.

The received and processed radiographic image is displayed on the portable information terminal 104 (step S908).

If the image managing unit 702 manages radiographic images including a radiographic image outputted from the radiography apparatus 102, a processed radiographic image, and a generated intermediate radiographic image, image processing may be selected so as to reduce a processing resource.

In step S902, the thumbnail of a radiographic image is transmitted with the examination information to the portable information terminal 104. If the acquisition of the thumbnail seriously interrupts the performance of the portable information terminal 104, the thumbnail of a selected past examination may be additionally requested from the central processing apparatus 202 when the examination is selected in the past examination list 803.

Third Embodiment

In a third embodiment, a case where an operator changes image processing parameters on a portable information terminal 104 after the first and second embodiments is described. The image processing parameters are, for example, the parameters of a luminance, a contrast, a noise reduction, a gray scale, and a window adjustment.

Figure 9:
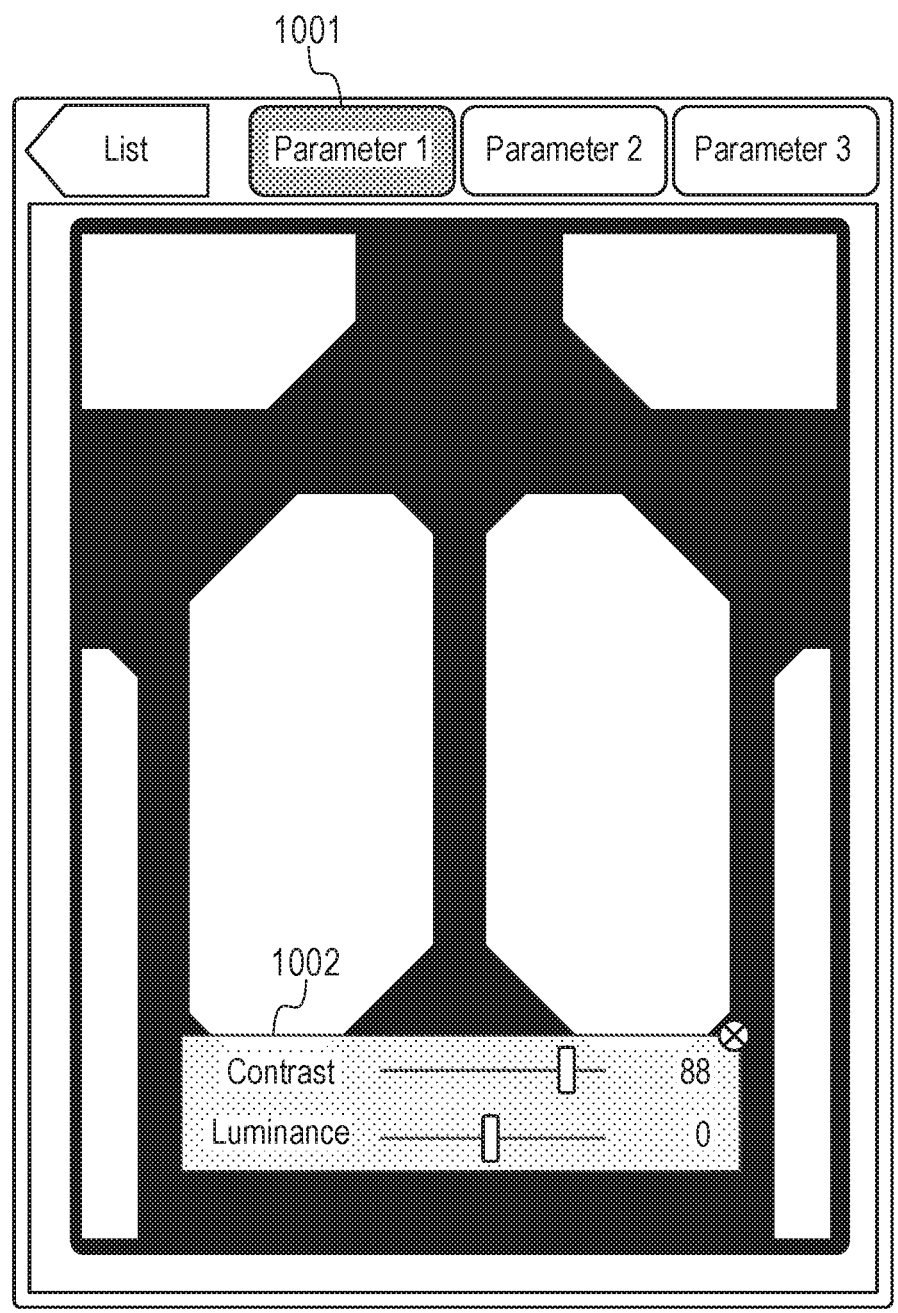
FIG. 9 illustrates an example of a GUI (a screen for changing image processing parameters) displayed on the portable information terminal.

FIG. 9 illustrates an example of a GUI (a screen for changing the image processing parameters) displayed on the portable information terminal 104. In this screen layout, when a parameter button 1001 is pressed, a parameter controller 1002 is displayed.

In FIG. 9, the parameter controller 1002 pops up to maximize the display area of an image. For the adjustment of the image processing parameters, the screen area of the parameter controller 1002 may be additionally set and the parameters may be adjusted by a scheme other than a slide bar.

Figure 10:
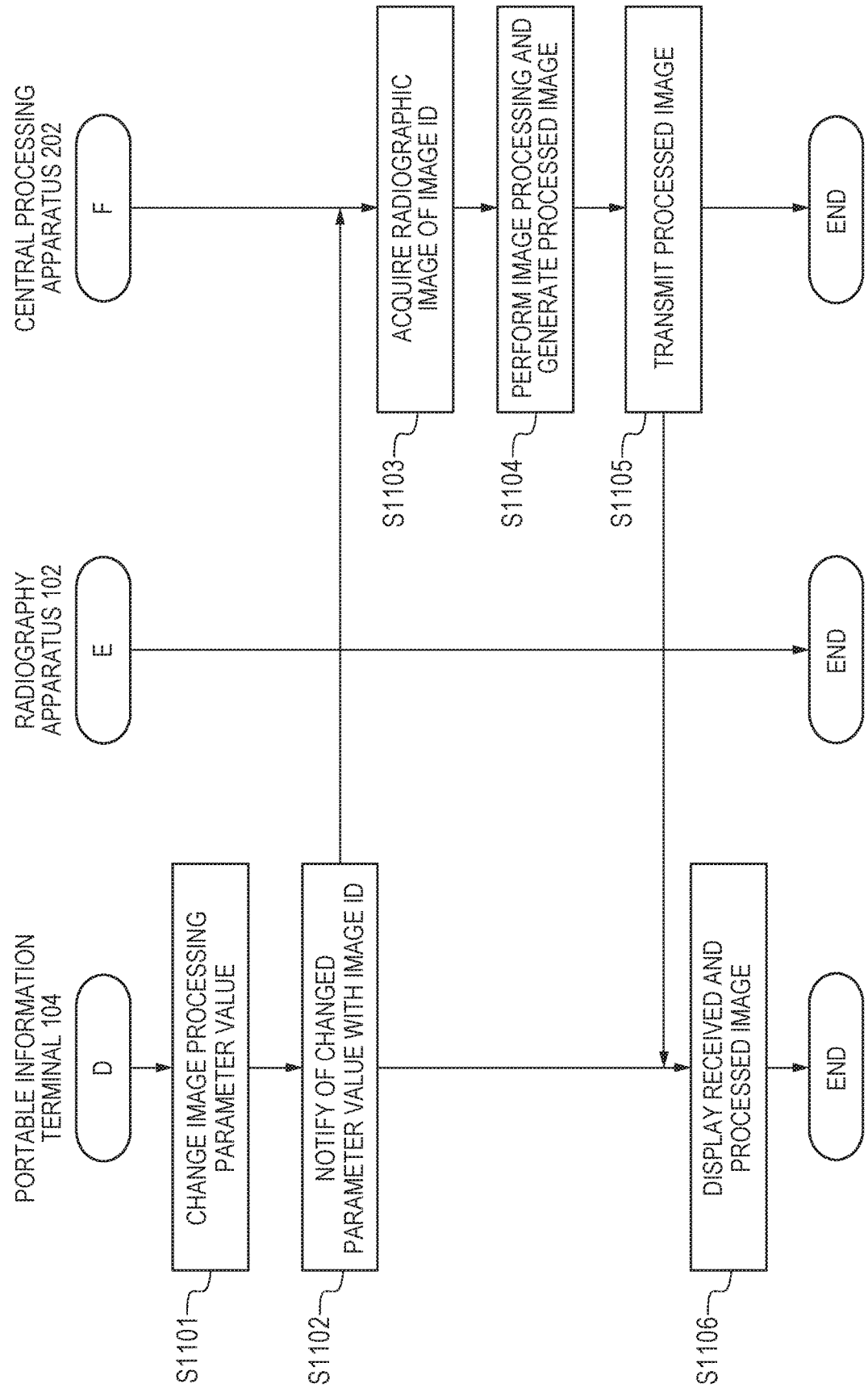
FIG. 10 is a flowchart showing an example of a processing flow of changing the image processing parameters.

FIG. 10 is a flowchart showing an example of a processing flow of changing the image processing parameters. In the processing flow of FIG. 10, a radiographic image outputted from a radiography apparatus 102 and an intermediate radiographic image are managed by an image managing unit 702. A parameter change is made to changeable parameter values for image processing on a radiographic image.

An operator changes a parameter value by using the parameter controller 1002 (step S1101). The portable information terminal 104 sets a predetermined image processing parameter for radiographic image data specified by an image ID. The portable information terminal 104 notifies a central processing apparatus 202 of the changed parameter value with the image ID and requests a parameter change (step S1102).

When receiving the request, the central processing apparatus 202 determines which one of the series of radiographic images for image processing is to be processed based on the contents of the parameter change. The central processing apparatus 202 acquires the radiographic image of the specified image ID from the image managing unit 702 (step S1103). The image managing unit 702 manages a radiographic image outputted from the radiography apparatus 102, a radiographic image processed by the central processing apparatus 202, and an intermediate radiographic image generated in the process of image processing, the radiographic images being associated with the same image ID.

For example, if the processing time of the intermediate radiographic image is shorter than that of the radiographic image outputted from the radiography apparatus 102, it is determined that the intermediate radiographic image is to be processed. The central processing apparatus 202 performs image processing on at least one of the radiographic image outputted from the radiography apparatus 102, the processed radiographic image, and the intermediate radiographic image according to the parameter, and then the central processing apparatus 202 transmits the radiographic image having undergone the image processing to the portable information terminal 104.

The central processing apparatus 202 performs image processing on the radiographic image again based on an image processing parameter stored as examination information, and generates a processed image (step S1104). The central processing apparatus 202 transmits the processed radiographic image to the portable information terminal 104 (step S1105). The central processing apparatus 202 performs image processing on radiographic image data according to a parameter set by the portable information terminal 104 and transmits the radiographic image data having undergone the image processing to the portable information terminal 104. The received and processed radiographic image is displayed on the portable information terminal 104 (step S1106). The portable information terminal 104 and the radiography apparatus 102 are associated with each other, the radiographic image is displayed on the portable information terminal 104, and the image processing parameters are changed, which may be performed as a series of processing as shown in FIGS. 4, 5, and 10.

Fourth Embodiment

In a fourth embodiment, it is described that a radiographic image is displayed by a plurality of portable information terminals.

Figure 11:
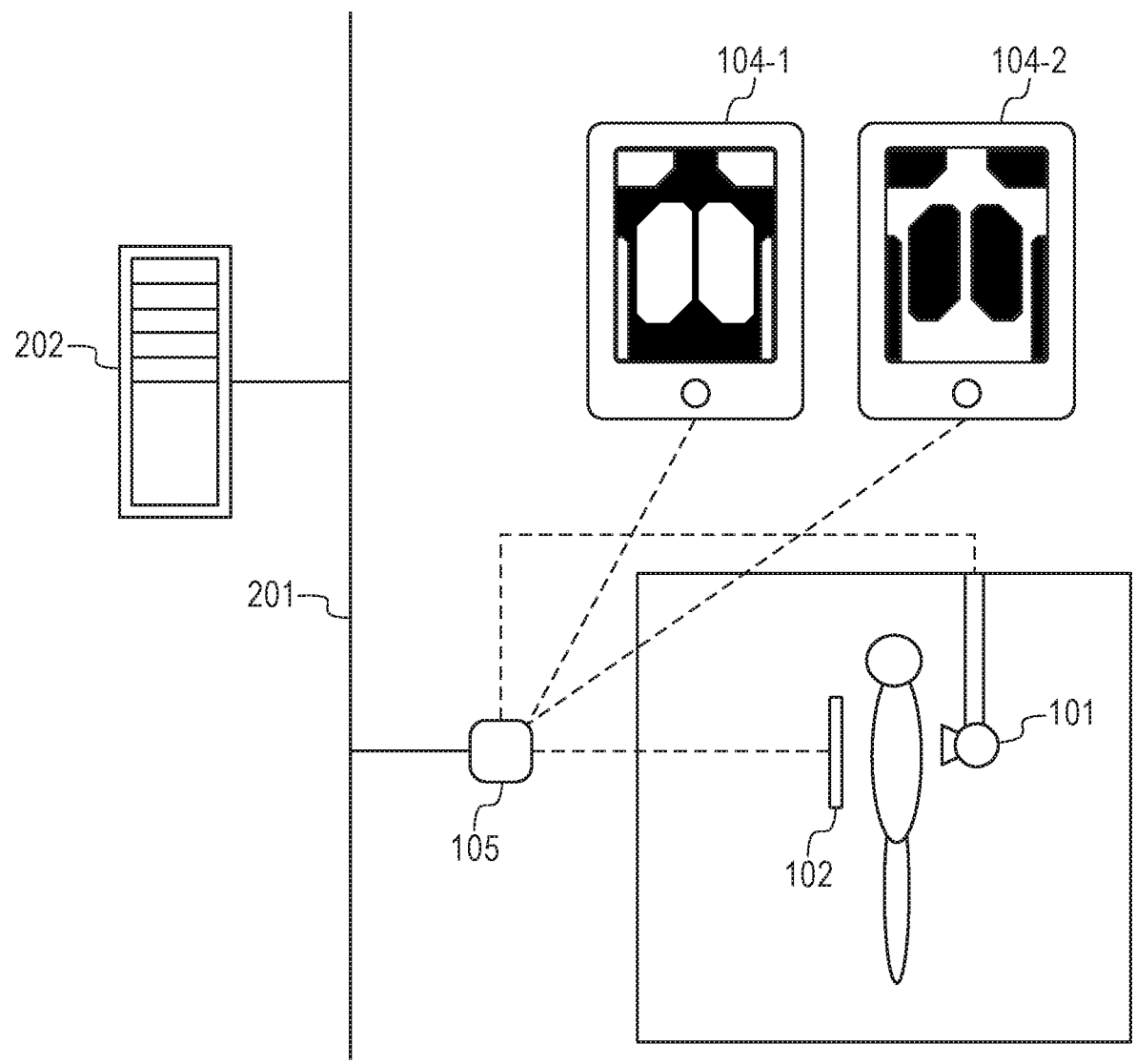
FIG. 11 is a block diagram illustrating an example of a configuration diagram of a radiography system according to a fourth embodiment of the present invention.

FIG. 11 is a block diagram illustrating an example of a configuration diagram of a radiography system according to a fourth embodiment. In FIG. 11, a radiography apparatus 102 is associated with a first portable information terminal 104-1 and a second portable information terminal 104-2. The radiography apparatus 102 has completed shooting.

The portable information terminals 104-1 and 104-2 can change the values of image processing parameters for the same radiographic image. The values of the image processing parameters are changed as in the third embodiment. The first portable information terminal 104-1 and the second portable information terminal 104-2, which are associated with a radiography apparatus 102-2, set a first parameter and a second parameter, respectively, for predetermined image processing on the same radiographic image data.

The central processing apparatus 202 performs first and second image processing on the same radiographic image data according to the set first and second parameters. The central processing apparatus 202 transmits first radiographic image data having undergone the first image processing to the first portable information terminal 104-1 and transmits second radiographic image data having undergone the second image processing to the second portable information terminal 104-2.

For example, different image processing parameters are inputted from the respective portable information terminals 104-1 and 104-2, image processing is performed on the same radiographic image according to the respective parameter values, and processed radiographic images are displayed on the portable information terminals 104-1 and 104-2, respectively.

Fifth Embodiment

In the first to fourth embodiments, the association managing unit 304 associates the portable information terminal 104 and the radiography apparatus 102. In a fifth embodiment, it is described that an association managing unit 304 can also associate a radiation generator 101 and a radiography apparatus 102. Multiple portable information terminals 104-1 and 104-2 can be associated with the radiation generator 101.

Figure 12:
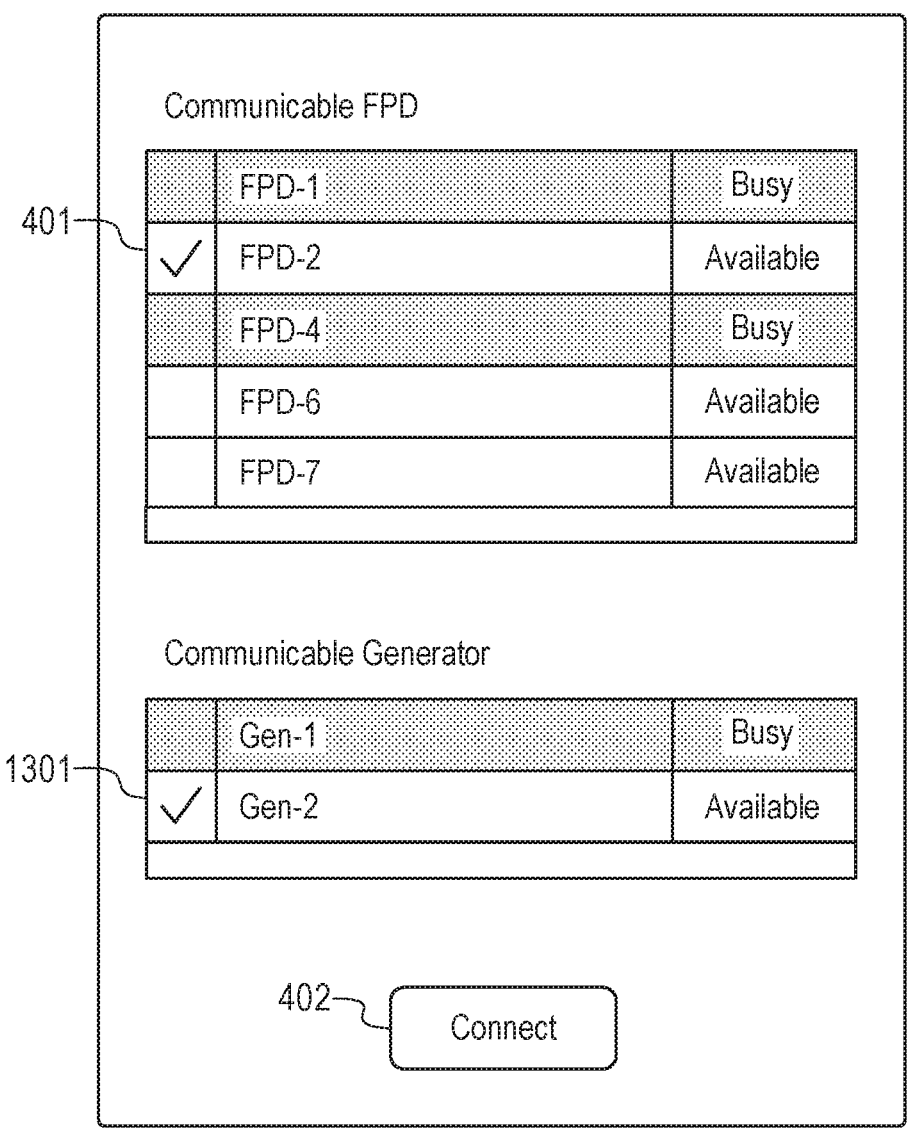
FIG. 12 illustrates an example of a GUI (a screen for selecting the radiography apparatus and a radiation generator to be associated with each other) displayed on a portable information terminal.

FIG. 12 illustrates an example of a GUI (a screen for selecting the radiography apparatus 102 and the radiation generator 101 to be associated with each other) displayed on a portable information terminal 104. In FIG. 12, the portable information terminal 104 displays a communicable radiation generator list 1301 in addition to the radiography apparatus list 401 shown in FIG. 4. The portable information terminal 104 selects the radiography apparatus 102 and the radiation generator 101 from the radiography apparatus list 401 and the radiation generator list 1301, respectively. Thus, the radiation generator 101, the radiography apparatus 102, and the portable information terminal 104 are associated with one another and operate as a single unit.

In the present embodiment, after the shooting of the radiography apparatus 102, the portable information terminal 104 may receive shooting information including a tube voltage and a tube current, etc. during radiation emission from the radiation generator 101. The portable information terminal 104 may include a GUI for operating the radiation generator 101 and change the shooting information. The portable information terminal 104 may include a command button for starting radiation emission and enable radiation emission from the GUI of the portable information terminal 104.

According to the first to fifth embodiments, multiple portable information terminals are associated with a radiation detecting unit so as to be managed by a processing unit. This improves portability and facilitates management including a change of the association.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A radiography system comprising:
   a plurality of radiation detecting units being detectable radiation;
   a plurality of portable information terminals allowed to be associated with a selected radiation detecting unit of the plurality of radiation detecting units; and
   a processing unit configured to manage association of the selected radiation detecting unit with at least one of the plurality of portable information terminals and associate the selected radiation detecting unit with the at least one of the plurality of portable information terminals in response to an instruction from an examiner using a portable information terminal in which a status relating to use of the plurality of radiation detecting units is displayed on a display unit,
   wherein the processing unit is further configured to receive and process radiographic image data obtained by the selected radiation detecting unit and transmit the processed radiographic image data to the at least one of the plurality of portable information terminals associated with the selected radiation detecting unit.

2. The radiography system according to claim 1, wherein the portable information terminal is configured to display the radiation detecting unit allowed to be associated with the portable information terminal and select the radiation detecting unit to be associated with the portable information terminal.

3. The radiography system according to claim 1, wherein the plurality of portable information terminals includes at least a first portable information terminal and a second portable information terminal, and
   wherein the first portable information terminal is capable of controlling, via the processing unit, association between the selected radiation detecting unit and the second portable information terminal.

4. The radiography system according to claim 3, wherein the first portable information terminal is capable of canceling, via the processing unit, the association between the selected radiation detecting unit and the second portable information terminal.

5. The radiography system according to claim 1, wherein in at least one of a case where shooting of a radiographic image by the selected radiation detecting unit is completed, a case where the selected radiation detecting unit is not operated for a predetermined time, a case where the selected radiation detecting unit is turned off, and a case where a network connection of the selected radiation detecting unit is cut off, the association between the selected radiation detecting unit and the at least one of the plurality of portable information terminals is canceled.

6. The radiography system according to claim 1, wherein the processing unit is configured to transmit at least one of radiographic image data outputted from the selected radiation detecting unit, radiographic image data processed by the processing unit, and intermediate radiographic image data generated in a process of the processing of the processing unit to the at least one of the plurality of portable information terminals in response to an image transmission request from the at least one of the plurality of portable information terminals associated with the selected radiation detecting unit.

7. The radiography system according to claim 6, wherein the at least one of the plurality of portable information terminals associated with the selected radiation detecting unit is configured to transmit the image transmission request to the processing unit based on past examination information.

8. The radiography system according to claim 1, further comprising:
   an ID issuing unit configured to issue an image ID to the processed radiographic image data; and
   an image managing unit configured to manage the processed radiographic image data associated with the image ID.

9. The radiography system according to claim 8, wherein the at least one of the plurality of portable information terminals is configured to set a predetermined image processing parameter, and
   the processing unit is configured to perform the image processing on the radiographic image data according to the set parameter and transmit the radiographic image data having undergone the image processing to the at least one of the plurality of portable information terminals.

10. The radiography system according to claim 9, wherein the image managing unit is configured to manage radiographic image data outputted from the selected radiation detecting unit and radiographic image data processed by the processing unit, the radiographic image data being associated with the same image ID.

11. The radiography system according to claim 1, wherein first and second portable information terminals associated with the selected radiation detecting unit are configured to set first and second parameters, respectively, for predetermined image processing on the same radiographic image data, and
   the processing unit is configured to perform first and second image processing on the same radiographic image data according to the set first and second parameters, transmit first radiographic image data having undergone the first image processing to the first portable information terminal, and transmit second radiographic image data having undergone the second image processing to the second portable information terminal.

12. The radiography system according to claim 1, wherein the plurality of portable information terminals is allowed to be associated with a radiation generating unit arranged to generate radiation.

13. The radiography system according to claim 1, wherein the status relating to use of the plurality of radiation detecting units is a status indicating an available state or a status indicating a busy state of each of the plurality of radiation detecting units.

14. A processing method comprising:
managing association of a selected radiation detecting unit of a plurality of radiation detecting units with at least one of a plurality of portable information terminals;
associating the selected radiation detecting unit with the at least one of the plurality of portable information terminals in response to an instruction from an examiner using a portable information terminal in which a status relating to use of the plurality of radiation detecting units is displayed on a display unit;
receiving and processing radiographic image data obtained by the selected radiation detecting unit; and
transmitting the processed radiographic image data to the at least one of the plurality of portable information terminals associated with the selected radiation detecting unit.

15. A non-transitory computer-readable storage medium storing a program that causes a processor to perform respective steps of the processing method according to claim 14 if the program is executed by the processor.

16. A processing apparatus comprising:
a processing unit configured to manage association of a selected radiation detecting unit of a plurality of radiation detecting units with at least one of a plurality of portable information terminals and associate the selected radiation detecting unit with the at least one of the plurality of portable information terminals in response to an instruction from an examiner using a portable information terminal in which a status relating to use of the plurality of radiation detecting units is displayed on a display unit,
wherein the processing unit is further configured to receive and process radiographic image data obtained by the selected radiation detecting unit and transmit the processed radiographic image data to the at least one of the plurality of portable information terminals associated with the selected radiation detecting unit.

17. The processing apparatus according to claim 16, wherein the plurality of portable information terminals includes at least a first portable information terminal and a second portable information terminal, and
wherein the first portable information terminal is capable of controlling, via the processing unit, association between the selected radiation detecting unit and the second portable information terminal.

18. The processing apparatus according to claim 16, wherein the status relating to use of the plurality of radiation detecting units is a status indicating available state or a status indicating busy state of each of the plurality of radiation detecting units.

* * * * *